United States Patent [19]

Hope

[11] Plant 4,342

[45] Dec. 12, 1978

[54] KALANCHOE PLANT NAMED TOLTEC

[75] Inventor: Claude Hope, Cartago, Costa Rica

[73] Assignee: Pan-American Plant Company, West Chicago, Ill.

[21] Appl. No.: 876,429

[22] Filed: Feb. 9, 1978

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler and Snow

[57] ABSTRACT

A new variety of kalanchoe plant most suitable for greenhouse culture as a pot plant and capable of year around flowering under photoperiod control conditions, characterized by its intense red florets which range from about 10 to 12 mm. in diameter, a uniform 10-week flowering response, a medium plant height with medium sized, glossy foliage, and an extended blooming period due to several weeks of continuous flower bud development.

1 Drawing Figure

BACKGROUND OF THE NEW PLANT

This new variety of kalanchoe originated as a seedling which resulted from my crossing Swiss Rose (unpatented) with Red Empress (unpatented) in the course of breeding efforts carried on by me at Cartago, Costa Rica, since 1969 with the object of producing new varieties of kalanchoe plants suitable for the potted plant market. This plant was selected by me for propagation because of the intense color of its flowers and asexual reproduction by cuttings from the original plant and subsequent propagation of the cultivar carried on by me through successive generations, by means of vegetative cuttings, at Cartago, Costa Rica, has demonstrated that the distinctive characteristics of the original plant hold true from generation to generation and appear to be fixed.

Propagation of this kalanchoe cultivar is now being done at West Chicago, Ill., and at Cortez, Fla., U.S.A., for the commercial market.

DESCRIPTION OF THE DRAWING

This new cultivar of kalanchoe is illustrated by the accompanying full color photographic drawing which shows a potted plant of the new variety in full bloom, the color rendition being as nearly true as it is reasonably possible to obtain by conventional professional photographic procedures.

DESCRIPTION OF THE NEW PLANT

The following is a detailed description of my new kalanchoe plant with color designations according to the R.H.S. Colour Chart published by The Royal Horticultural Society of London, England, in collaboration with the British Colour Council.

THE PLANT

Origin: Seedling.

Parentage:

*Seed parent.*—Swiss Rose (unpatented).

*Pollen parent.*—Red Empress (unpatented).

Classification:

*Botanic.*—*Kalanchoe blossfeldiana.*

*Commercial.*—Kalanchoe pot plant.

Form: Bush.

Height: 18 to 26 cm.

Growth: Upright and sturdy, with good strength and medium vigor.

Branching: Normal, under natural conditions.

Foliage:

*Leaf size.*—Medium, about 5.5 to 11 cm. long and about 3.5 to 5.0 cm. wide.

*Leaf shape.*—Ovate, with an obtuse tip and generally dentate margins. Surface aspect: Glossy. Venation: Pinnate. Color: Upper side — 147A. Under side — 147B. Petioles: About 15 to 29 mm. long.

THE BUD

Shape: Generally-long cylindrical with a rather obtuse tip before opening.

Size:

*Diameter.*—About 1.75 mm.

*Length.*—About 9 to 11 mm.

Opening rate: Rapid — but opens fully within 1 day.

Sepals: Number — four or five surrounding the receptacle.

*Appearance.*—Spear-shaped and upstanding.

*Surface texture.*—Smooth.

*Aspect.*—Shiny.

*Color.*—Inside — 144A. Outside — 144A.

THE FLOWER

Flowering: 10-week response with photoperiod control. Capable of year around flowering.

*Natural season.*—November through January under Costa Rican conditions.

Blooms: Flower type — regular and complete.

*Borne.*—Corymbos on a compound cyme.

*Size.*—Small, about 10 to 12 mm. wide and about 9 to 11 mm. in depth.

*Shape.*—Generally flat when first opening, the petals reflexing as the bloom matures.

*Petals.*—Four or five per flower, each separate and distinct. Form: Nearly oval. About 5 to 6 mm. long and about 3.5 mm. wide. Texture: Firm. Appearance: Shiny. Color: Upper side — 40A and 42A with color 1A at the base. Under side — 39B and 179C. Tonality of florescence at distance of 8 feet: 41A. Discoloration: Moderate fade after full bloom.

Peduncle: Sturdy and upright.

*Surface texture.*—Smooth.

*Color.*—146C.

Persistence: Flowers hang on and dry.

Effect of weather: None. This variety is recommended only for greenhouse culture.

Disease resistance: This plant has been observed to resist powdery mildew in environments where that disease is present.

Fragrance: Typical kalanchoe. Lasting quality: Approximately 4 weeks.

REPRODUCTIVE ORGANS

Stamens: Number — 8 to 10.

*Anthers.*—Color — Yellow.

*Filaments.*—Color — Yellow-Green.

*Pollen.*—Color — Yellow.

Pistils: Number four or five.

*Stigmas.*—Color — Initially Yellow-Green, becoming Off-White as flower ages.

*Ovaries.*—4 to 5 in number, each developing multiple seeds.

This new kalanchoe cultivar is characterized particularly by its intense red florets which exhibit only moderate fading during the florescence period, the blooms ranging from about 10 to 12 mm. in diameter and flowering for an extended period due to continuous flower bud development over a period of several weeks.

The kalanchoe "Toltec" herein shown and described is a sister plant to the variety "Goddess" disclosed and claimed in my copending application Ser. No. 876,428, filed of even date herewith, both plants having been bred from the same parents. The following table is intended to show the differences of the two plants from each other.

| | "Goddess" | "Toltec" |
|---|---|---|
| Plant: | | |
| Height: | 17–22 Cm. | 18–26 Cm. |
| Growth: | Strong with medium vigor. | Good strength; medium vigor. |
| Branching: | Normal | Normal |
| Foliage: | | |
| Size of Leaf: | | |
| Length: | 5.5–12 Cm. | 5.5–11 Cm. |
| Width: | 3–5.5 Cm. | 3.5–5 Cm. |
| Shape of Leaf: | Elliptical | Ovate |
| Color: | | |
| Upper Side: | 146A | 147A |
| Under Side: | 146B | 147B |
| Florescence: | | |
| Response: | 10-week | 10-week |
| Bud Size: | | |
| Diameter: | 1.75 mm. | 1.75 mm. |
| Length: | 6–7 mm. | 9–11 mm. |
| Flower Size: | | |
| Diameter: | 10–12 mm. | 10–12 mm. |
| Depth: | 8–10 mm. | 9–11 mm. |
| Borne: | On a compound cyme. | Corymbos on a compound cyme. |
| Color of Petals: | | |
| Upper Side: | 57B–46C at base. | 40A and 42A; base 1A. |
| Under Side: | 55C | 39B and 179C |
| Tonality at 8 Ft.: | 52A | 41A |

I claim:

1. A new and distinct cultivar of kalanchoe substantially as herein shown and described, characterized by the intense red coloring of its flowers, its continuous production of flowers over an extended period, and its attractive pot-size growth habit.

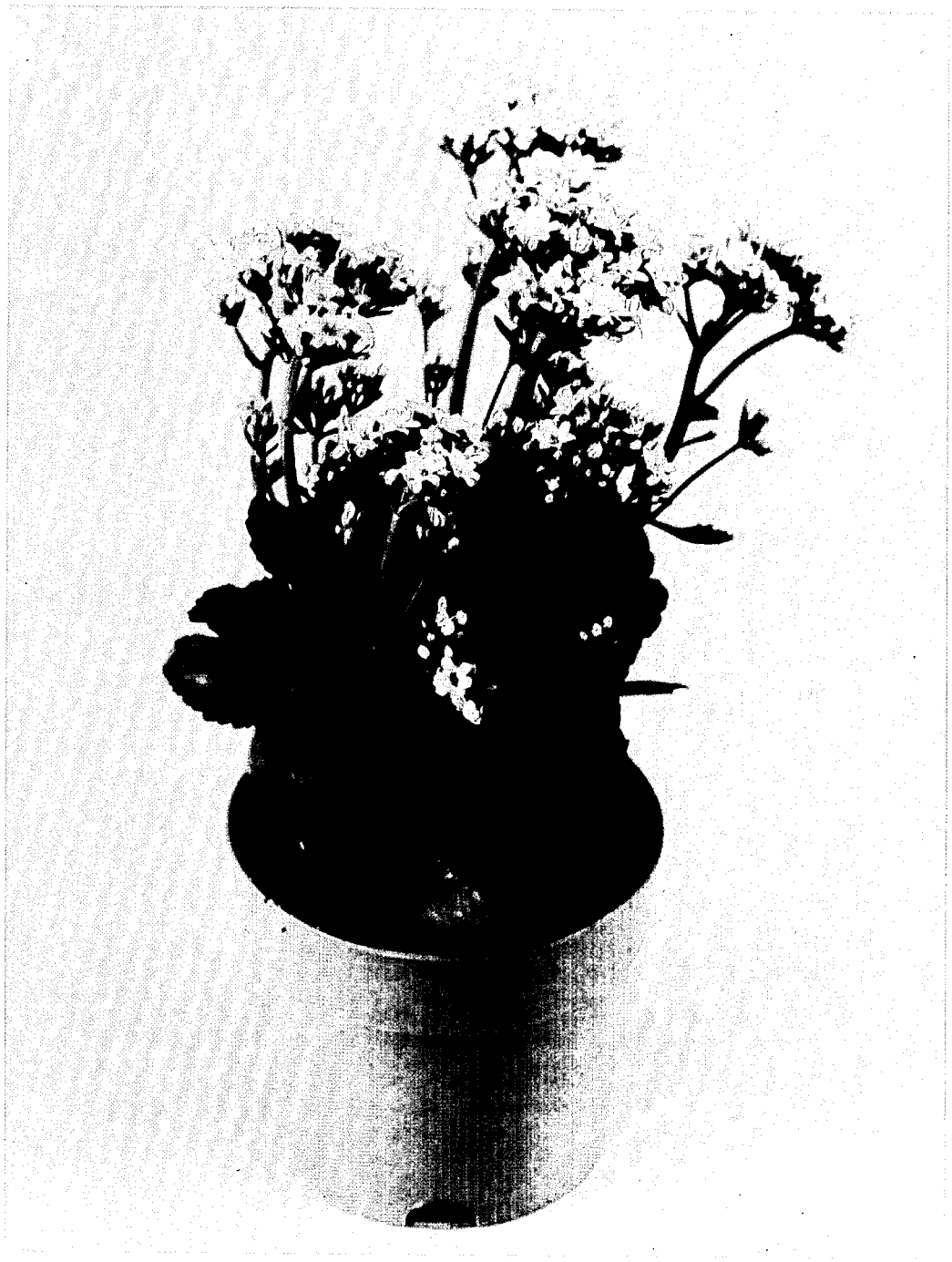

* * * * *